United States Patent [19]
Liu et al.

[11] Patent Number: 6,120,794
[45] Date of Patent: *Sep. 19, 2000

[54] EMULSION AND MICELLAR FORMULATIONS FOR THE DELIVERY OF BIOLOGICALLY ACTIVE SUBSTANCES TO CELLS

[75] Inventors: Dexi Liu; Feng Liu; Jing-Ping Yang, all of Pittsburgh; Leaf Huang, Wexford, all of Pa.

[73] Assignee: University of Pittsburgh, Pittsburgh, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/534,180

[22] Filed: Sep. 26, 1995

[51] Int. Cl.$^7$ ............................ A61K 9/107; A61K 9/127
[52] U.S. Cl. ............................ 424/450; 424/400; 514/44; 514/938; 935/54
[58] Field of Search ........................... 424/450, 400; 514/44, 938; 935/54

[56] References Cited

U.S. PATENT DOCUMENTS

| | | |
|---|---|---|
| 4,544,545 | 10/1985 | Ryan et al. . |
| 4,897,355 | 1/1990 | Eppstein et al. . |
| 4,958,013 | 9/1990 | Letsinger . |
| 5,043,164 | 8/1991 | Huang et al. . |
| 5,100,662 | 3/1992 | Bolcsak et al. . |
| 5,264,618 | 11/1993 | Felgner et al. . |
| 5,279,833 | 1/1994 | Rose . |
| 5,283,185 | 2/1994 | Epand ................................ 435/172.3 |
| 5,286,634 | 2/1994 | Stadler ................................ 435/172.3 |
| 5,334,761 | 8/1994 | Gebeyehu et al. . |
| 5,366,737 | 11/1994 | Eppstein et al. . |
| 5,374,548 | 12/1994 | Caras . |
| 5,523,222 | 6/1996 | Page et al. . |
| 5,540,933 | 7/1996 | Ruoslahti et al. . |
| 5,545,412 | 8/1996 | Eppstein et al. . |
| 5,578,475 | 11/1996 | Jesse ................................ 435/172.3 |
| 5,635,487 | 6/1997 | Wolf ................................ 514/44 |
| 5,661,025 | 8/1997 | Szoka, Jr. et al. . |
| 5,705,385 | 1/1998 | Bally ................................ 435/320.1 |
| 5,795,587 | 8/1998 | Gao et al. . |
| 5,844,107 | 12/1998 | Hanson et al. . |
| 5,877,302 | 3/1999 | Hanson et al. . |
| 5,885,613 | 3/1999 | Holland ................................ 424/450 |
| 5,972,900 | 10/1999 | Ferkol, Jr. et al. . |
| 5,972,901 | 10/1999 | Ferkol, Jr. et al. . |
| 6,008,202 | 12/1999 | Huang et al. . |
| 6,008,336 | 12/1999 | Hanson et al. . |

FOREIGN PATENT DOCUMENTS

| | | |
|---|---|---|
| 0 387 647 | 3/1990 | Germany . |
| 0 387 647 A2 | 3/1990 | Germany . |
| WO 93/05162 | 3/1993 | WIPO . |
| WO 93/18852 | 9/1993 | WIPO . |
| WO 95/12384 | 5/1995 | WIPO . |
| WO 96/22765 | 8/1996 | WIPO . |

OTHER PUBLICATIONS

Behr et al. (Sep. 1989). "Efficient gene transfer into mammalian primary endocrine cells with lipopolyamine-coated DNA," *Proc. Natl. Acad. Sci. USA* 86:6982–6986.

(List continued on next page.)

*Primary Examiner*—Gollamudi S. Kishore
*Attorney, Agent, or Firm*—Morrison & Foerster LLP

[57] ABSTRACT

New emulsion and micelle formulations are described as are complexes of these formulations with biologically active substances. The novel formulations are different from cationic lipid vectors such as cationic liposomes in that the complexes formed between biologically active substances and the emulsion and micellar formulations of this invention are physically stable and their transfection activity is resistant to the presence of serum. These novel formulations are disclosed to be useful in areas such as gene therapy or vaccine delivery.

21 Claims, 6 Drawing Sheets

OTHER PUBLICATIONS

Cheetham et al. (1990). "Cholesterol sulfate inhibits the fusion of sendai virus to biological and model membranes," *J. Biol. Chem.* 256:12404–12409.

Demeneix. (Mar. 1994). "Temporal and spatial expression of lipospermine–compacted genes transferred into chick embryos in vivo," *BioTechniques* 16:496–501.

Felgner et al. (Nov. 1987). "Lipofection: A highly efficient, lipid–mediated DNA–transfection procedure," *Proc. Natl. Acad. Sci. USA* 84:7413–7417.

Gao et al. (1991). "A novel cationic liposome reagent for efficient transfection of mammalian cells," *Biochem. Biophy. Res. Commun.* 179(1):280–285.

Hui et al. (Nov. 1994). Induction of alloreactive cytotoxic T lymphocytes by intrasplenic immunization with allogenic class I major histocompatiblity complex DNA and DC–chol cationic liposomes, *J. Liposome Res.* 4(3):1077–1078.

Letsinger et al. (Sep. 1989). "Cholesteryl–conjugated oligonucleotides: Synthesis, properties, and activity as inhibitors of replication of human immunodeficiency virus in cell culture," *Proc. Natl. Acad. Sci. USA* 86:6553–6556.

Malone. (1989). "Cationic liposome–mediated RNA transfection," *Proc. Natl. Acad. Sci. USA* 86:6077–6081.

Philip et al. (1993). "In vivo gene delivery" *J. Biol. Chem.* 268(22):16087–16090.

Pinnaduwage. (1989). "Use of a quaternary ammonium detergent in liposome mediated DNA transfection of mouse L–cells," *Biochim. Biophys. Acta* 985(1):33–37.

Rajaonarivony et al. (Sep. 1993). "Development of a new drug carrier made from alginate," *J. Pharm. Sci.* 82(9):912–917.

Rose et al. (Apr. 1999). "A new cationic liposome reagent mediating nearly quantitative transfection of animal cells," *BioTechniques* 10:520–525.

Stamatatos et al. (1988). "Interactions of cationic lipid vesicles with negatively charged phospholipid vesicles and biological membranes," *Biochemistry* 27:3917–3925.

Sternberg. (1994). "New structures in complex formation between DNA and cationic liposomes visualized by freeze–fracture electron microscopy," *FEBS Lett.* 356:361–366.

Stewart et al. (Jun. 1992). "Gene transfer in vivo with DNA–liposome complexes: Safety and acute toxicity in mice," *Hum. Gene Ther.* 3:267–275.

Stribling et al. (Dec. 1992). "Aerosol gene delivery in vivo" *PNAS USA* 89:11277–11281.

Zhou (1991). "Lipophilic polylysines mediate efficient DNA transfection in mammalian cells," *Biochim. Biophys. Acta* 1065(1):8–14.

Patent Abstracts of japan, vol. 18. No. 337 (c–1217), Jun. 27, 1994 and Database WPI, Section Ch, Week 9416, Derwent Publications Ltd., London, GB; Class B–05, AN 94–131963 (1996).

Chemical Abstracts, vol. 121, No. 9, Aug. 29, 1994, Columbus, Ohio, US; abstract No. 109565, Yamada, H.: "Preparation of liposomes containing glycosides".

J. Colloid Interface Sci., vol. 125, No. 1, 1988, pp. 261–270, XP000645802, Treiner C., et al., "Micellar solubilization in aqueous binary surfactant systems : barbituric acids in mixed anionic+nonionic or cationic+nonionic mixtures".

Biochim, Biophys. Acta., vol. 1111, No. 2. 1992, pp. 239–246, XP000607577, Farhood H. et al., "Effect of cationic cholesterol derivatives on gene transfer and protein kinase C activity".

Biochemestry, vol. 31, 1992, pp. 9025–9030, XP000645334, Bottega R. et al; "Inhabition of protein kinase C by cationic amphiphiles".

EMULSION AND MICELLAR FORMULATIONS FOR THE DELIVERY OF BIOLOGICALLY ACTIVE SUBSTANCES TO CELLS

FIELD OF THE INVENTION

The present invention relates to the use of lipid dispersions to deliver biologically active substances to cells. In particular, the present invention relates to emulsion and micellar formulations and to the ability of these formulations to form stable complexes with biologically active substances and thereby facilitate the delivery of these substances to cells.

BACKGROUND OF THE INVENTION

Cationic liposomes are of interest as a non-viral vehicle for the delivery of biologically active substances such as drugs, hormones, enzymes, nucleic acids and antigens, including viruses, to cells both in vitro and in vivo. Indeed, cationic liposomes have been demonstrated to deliver genes in vivo (Nabel, E. G., et al. (1990) *Science*, 249: 1285–1288), (Brigham, K. L., et al. (1989) *Am. J. Respir. Cell Mol. Biol.*, 195–200, Stribling, R., et al. (1992) *Proc. Natl. Acad. Sci. U.S.A.*, 89: 11277–11281), (Plautz, G. E., et al. (1993) *Proc. Natl. Acad. Sci. U.S.A.*, 90: 4645–4649, Stewart, M. J., et al. (1992) *Hum. Gene Ther.*, 3: 267–275). However, the inhibition by serum components of the transfer of nucleic acids by cationic liposomes limits the application of liposomes as a vector for nucleic acids in vivo to regional administrations which avoid exposure to serum.

In addition, stability is a major problem limiting the use of liposomes, both in terms of shelf life and after administration in vivo. Thus, it is desirable to explore the use of other types of lipid dispersions as delivery systems utility for biologically active substances.

U.S. Pat. No. 4,610,888 refers to the use as a drug-delivery system of water-in-oil emulsions in which the volume of aqueous phase ranges from about 0.70%. to about 10.25% of the volume of the lipid components used. However, such water-in-oil emulsions are unsuitable for delivering substances in blood or in other aqueous body tissues.

SUMMARY OF INVENTION

The present invention relates to novel emulsion and micellar formulations useful for delivering biologically active substances to cells. The emulsion and micellar formulations of this invention are compatible with blood, retain activity in the presence of serum and are stable in storage. The emulsions of this invention comprise lipid components and an aqueous carrier, where the lipid components comprise an oil component, a cationic amphiphile component, preferably a cationic lipid, and a nonionic surfactant component. The micellar-formulations comprise lipid components and an aqueous carrier, where the lipid components comprise a cationic amphiphile component and a nonionic surfactant component. The lipid components of the emulsion and micellar formulation of the present invention may further comprise a neutral phospholipid component.

"Component" as used throughout the specification and claims is defined as: comprising at least one cationic amphiphile or a mixture of amphiphiles when used in the phrase "amphiphile component"; comprising at least one oil or a mixture of oils when used in the phrase "oil component"; comprising at least one nonionic surfactant or a mixture of nonionic surfactants when used in the phrase "nonionic surfactant component"; comprising at least one neutral phospholipid or a mixture of neutral phospholipids when used in the phrase "neutral phospholipid component".

The invention further relates to complexes formed by combining biologically active substances and the above-identified emulsion and micellar formulations. These biologically active substance:emulsion and biologically active substance:micelle complexes are stable over time and may have therapeutic and/or prophylactic utility in vivo depending on the activity of the biologically active substance contained in the complex.

This invention also provides a method for delivering a biologically active substance to cells by exposing cells to the complexes of this invention. In one embodiment, a method of exposing cells to a biologically active substance is provided, said method comprising culturing said cells in the presence of a biologically active substance:emulsion complex or a biologically active substance:micelle complex thereby facilitating delivery of the biologically active substance to cells.

The invention further provides a method of delivering a biologically active substance to cells in vivo comprising administering to an animal or human the complexes of this invention. It is to be understood that the complexes used for the delivery of biologically active substances to cells in vitro or in vivo may be freshly prepared by admixture or may be prepared earlier and stored prior to their use.

The invention further relates to a kit containing an emulsion or micellar formulation of the present invention. The invention also provides a kit containing a complex formed between a biologically active substance and an emulsion or micellar formulation of the present invention.

Methods for producing emulsion and micellar formulations according to the invention are also provided herein.

In one embodiment, a method for producing an emulsion formulation of this invention comprises a) combining an organic solvent with an oil component, a cationic amphiphile component and a nonionic surfactant component;

b) removing the organic solvent to leave a lipid film; and c) suspending the lipid film in an aqueous carrier to produce said emulsion formulation miscible in aqueous solution.

In an alternative embodiment, the oil may serve as the organic solvent in step (a) such that the method for producing an emulsion formulation of this invention comprises a) combining an oil component, a cationic amphiphile component and a nonionic surfactant component; and b) adding an aqueous carrier to the combination of step (a).

When a neutral phospholipid component is to be included in the emulsion, the neutral phospholipid component is combined with the above components in step (a).

The method for producing a micellar formulation miscible in aqueous solution comprises:

a) combining an organic solvent with a cationic amphiphile component and a nonionic surfactant component;

b) removing the organic solvent to leave a lipid film; and c) suspending the lipid film in an aqueous carrier to produce said micellar formulation miscible in aqueous solution.

When a neutral phospholipid component is to be included in the micellar formulation, the neutral phospholipid component is combined with the above components in step (a).

DETAILED DESCRIPTION OF INVENTION

Figure 1:
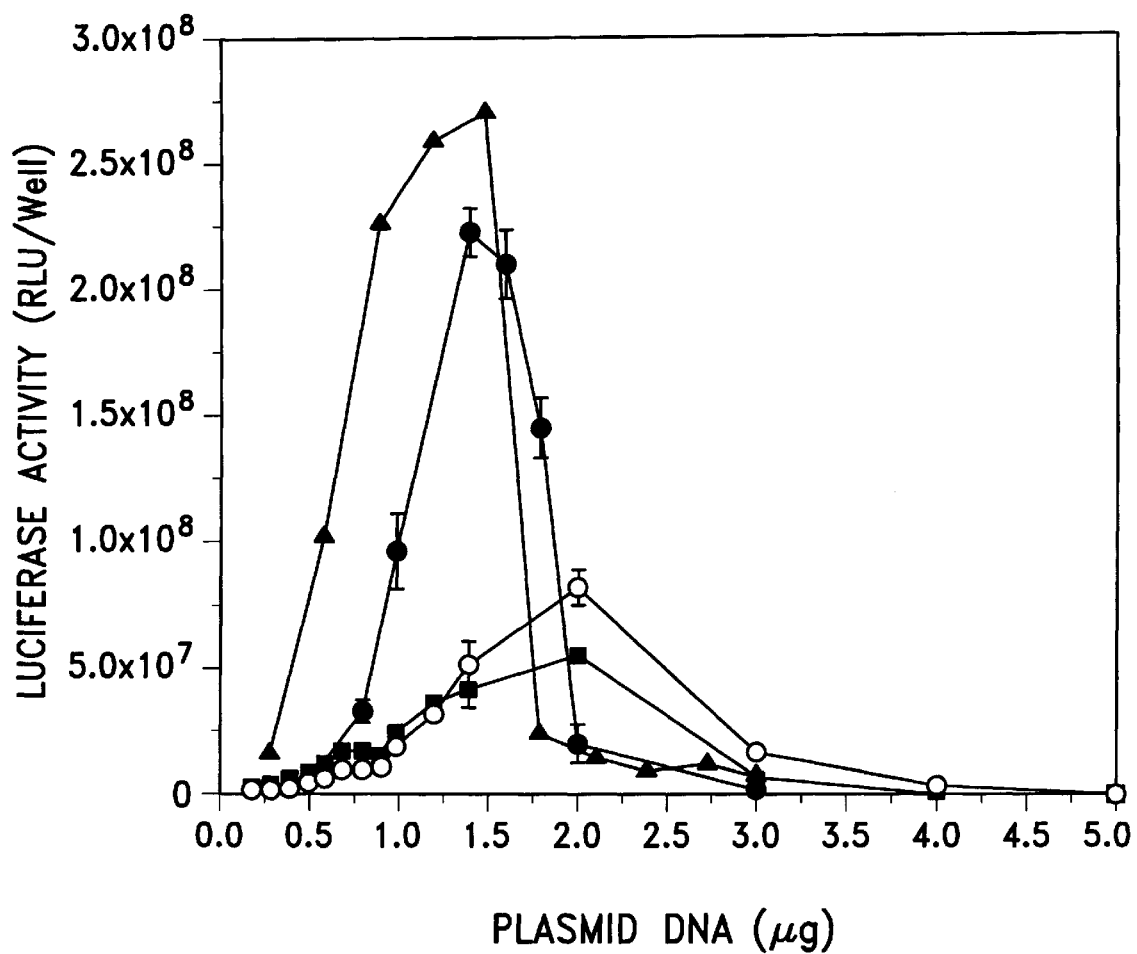
FIG. 1 shows the optimization of transfection of BL6 cells with complexes formed between pCMV-Luc DNA and formulations #21 (●—●), #27 (■—■), #28 (▲—▲) or #30 (○—○) (see Table 3 for compositions of formulations) by mixing 6 µl of each formulation (6 µl of each formulation contained 4.5 µg of DC-Chol) with varying amounts of pCMV-Luc DNA as indicated on the horizontal axis.

The present invention relates to emulsion and micellar formulations which form stable complexes with biologically active and thereby facilitate the delivery of the biologically active substances to cells.

The emulsion formulations of this invention are oil-in-water emulsions which comprise an aqueous carrier and the following lipid components, an oil component, a cationic amphiphile component, a nonionic surfactant component and optionally, a neutral phospholipid component.

Preferably, the total lipid components are present in the emulsion formulation in an amount from about 0.001 to about 20% by weight, more preferably from about 0.01 to about 10% by weight and most preferably from about 0.05 to about 2% by weight, with the remainder of the emulsion by weight being aqueous carrier. Thus, for example, for formulation #1 in Table 1 where 0.625 mg of total lipid components are present in 0.5 ml of PBS, the weight % of total lipid components in formulation #1 can be calculated as follows: Assuming 1 ml of PBS, like 1 ml of water, weighs approximately 1000 mg, then 0.5 ml of PBS weighs 500 mg and the weight % of total lipid components contained in formulation #1 is $$\frac{0.625 \text{ mg}}{0.625 \text{ mg} + 500 \text{ mg}} \times 100 = 0.125\%.$$

Of the total lipid components present in the emulsion formulations of this invention, preferably, the amphiphile component is present in an amount from about 5 to about 80 weight % of the total lipid components in the emulsion formulation; the oil component is present in an amount from about 10 to about 80 weight % of the total lipid components; the nonionic surfactant component is present in an amount from about 5 to about 50 weight % of the total lipid components, and optionally, the neutral phospholipid component is present in the formulation in an amount from about 5 to about 25 weight % of the total lipid component.

More preferably, the oil component is present in an amount from about 10–60 weight % of the total lipid components in the emulsion formulation; the amphiphile component is present in an amount from about 20–60 weight % of the total lipid components; the nonionic surfactant component is present in an amount from about 10–50 weight % of the total lipid components and optionally, a neutral phospholipid component is present in amount from about 10–40 weight % of the total lipid components.

Most preferably, the emulsion formulation comprises the oil component in amount from about 10–20 weight % of the total lipid components; the amphiphile component in an amount from about 40–60 weight % of the total lipid components; the nonionic surfactant component in an amount from about 20–50 weight % of the total lipid components and optionally, the neutral phospholipid component in an amount from about 10–20 weight % of the total lipid components. A particularly preferred emulsion formulation contains an oil, a cationic amphiphile, a nonionic surfactant and a neutral phospholipid in a weight ratio of about 2:6:1:2.

The micellar formulations of this invention are compatible with blood. The micellar formulations comprise an aqueous carrier and the following lipid components: a cationic amphiphile component, a nonionic surfactant component and optionally, a neutral phospholipid component.

Preferably, the total lipid components are present in the micellar formulation in an amount ranging from about 0.0001 to about 700 by weight, more preferably from about 0.001 to about 600% by weight and most preferably from about 0.001 to about 50 by weight, with the remainder by weight of the micellar formulation being aqueous carrier. Thus, for example, for formulation #15 in Table 2 where 1.25 mg of total lipid components are present in 1 ml of PBS, the weight % of total lipid components in formulation #15 can be calculated as follows: Assuming 1 ml of PBS, like 1 ml of water, weighs approximately 1000 mg, then the weight % of total lipid components in formulation #15 is $$\frac{1.25 \text{ mg}}{1.25 \text{ mg} + 1000 \text{ mg}} \times 100 = 0.125\%.$$

Of the total lipid components contained in the micellar formulations of this invention, preferably, the amphiphile component is present in an amount from about 10 to about 90 weight % of the total lipid components in the micellar formulation, the nonionic surfactant component is present in an amount from about 10 to about 90 weight % of the total lipid components; and optionally, the neutral phospholipid component is present in an amount from about 5 to about 40 weight % of the total lipid components.

More preferably, the amphiphile component is present in an amount from about 30 to about 90 weight % of the total lipid components in the micellar formulation, the nonionic surfactant component is present in an amount from about 10 to about 70 weight % of the total lipid components and optionally, the neutral phospholipid component is present in an amount from about 5 to about 30 weight % of the total lipid components.

Most preferably, the amphiphile component is present in an amount from about 50 to about 90 weight % of the total lipid components in the micellar formulation, the nonionic surfactant component is present in an amount from about 10 to about 50 weight % of the total lipid components and optionally, the neutral phospholipid component is present in an amount from about 10 to about 20 weight % of the total lipid components. A particularly preferred micellar formulation contains a cationic amphiphile, a nonionic surfactant and a neutral phospholipid in a weight ratio of about 6:1:2.

By oil component as used herein is meant any water immiscible component that is conventionally referred to as an oil. It is understood that the oil component may include mixtures of two or more oils. Examples of oils which can be used to produce the emulsion formulations of the present invention include, but are not limited to, natural oils such as almond oil, coconut oil, cod liver oil, corn oil, cottonseed oil, castor oil, olive oil, palm oil, peanut oil, peppermint oil, rose oil, safflower oil, sesame oil, soybean oil, sunflower oil and vegetable oil and synthetic oils such as triethylglycerol and diethylglycerol. A preferred oil is castor oil.

The cationic amphiphile component of the formulations of this invention may be any cationic amphiphile or mixture of amphiphiles which is effective for use in liposomes or for producing lipid complexes capable of delivering a biologically active substance to cells. For example, the amphiphiles described in Bolcsak et al U.S. Pat. No. 5,100,662, which is incorporated herein by reference, would be suitable for use in this invention. Additional examples of cationic amphiphiles suitable for formulating the emulsion and micellar formulations of this invention include, but are not limited to, cationic lipids such as 1, 2 bis(oleoyloxy)-3-(trimethylammonio) propane (DOTAP); N-[1, -(2,3-dioleoyloxy) propyl]-N, N, N-trimethyl ammonium chloride (DOTMA) or other N-(N, N-1-dialkoxy)-alklyl-N, N, N-trisubstituted ammonium surfactants; 1, 2 dioleoyl-3-(4'-trimethylammonio) butanoyl-sn-glycerol (DOBT) or cholesteryl (4' trimethylammonia) butanoate (ChOTB) where the trimethylammonium group is connected via a butanoyl spacer arm to either the double chain (for DOTB) or cholesteryl group (for ChOTB); DORI (DL-1, 2-dioleoyl-3-dimethylaminopropyl-B-hydroxyethylammonium) or DORIE (DL-1, 2-O-dioleoyl-3-dimethylaminopropyl-β-hydroxyethylammonium) (DORIE) or analogs thereof as disclosed in WO 93/03709, incorporated herein by reference; 1, 2-dioleoyl-3-succinyl-sn-glycerol choline ester (DOSC); cholesteryl hemisuccinate ester (ChOSC); lipopolyamines such as doctadecylamidoglycylspermine (DOGS) and dipalmitoyl phosphatidyesthanolamidospermine (DPPES) or the cationic lipids disclosed in U.S. Pat. No. 5,283,185, incorporated herein by reference, cholesteryl-3β-carboxyl-amido-ethylenetrimethylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamido-ethylenetrimethylammonium iodide, 1-dimethylamino-3-trimethylammonio-DL-2-propyl-cholesteryl-3β-oxysuccinate iodide, 2-[(2-trimethylammonio)-ethylmethylamino] ethyl-cholesteryl-3β-oxysuccinate iodide, 3β[N-(N', N'-dimethylaminoethane) carbamoyl] cholesterol (DC-Chol), and 3β-[N-(polyethyleneimine)-carbamoyl]cholesterol.

Examples of preferred amphiphiles include cholesteryl-3β-carboxyamidoethylenetri-methylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)ethylmethylamino]ethyl-cholesteryl-3β-oxysuccinateiodide, 3β[N-(N', N'dimethyl-aminoethane)-carbamoyl]-cholesterol (DC-Chol), and 3β[N-(polyethyleneimine)-carbamoyl]cholesterol.

Since an attribute of the emulsion and micellar formulations of the present invention is their stability when stored alone or as complexes with biologically active substances, it will be understood by those of ordinary skill in the art that preferred cationic amphiphiles are cationic lipids in which bonds between the lipophilic group and the amino group are stable in aqueous solution. Such bonds include amide bonds, ester bonds, ether bonds and carbamoyl bonds. A more preferred cationic lipid is DC-Chol.

The nonionic surfactant component of the formulations of this invention includes at least one nonionic surfactant of a molecular weight between 200 and 20,000. In one embodiment, these surfactants may be formed by reacting a hydrophobic hydroxyl-containing compound (e.g., an alcohol or phenol) with ethylene oxide where the number of ethylene oxide groups may be added to any desired extent. However, those of ordinary skill in the art would understand that the ability to stabilize the emulsions or micelles of this invention may depend on the relative amount of ethylene oxide added to a given hydrophobic group. It is further understood that surfactants having branched chain ethylene oxide moieties cover more surface area than surfactants having single chain ethylene oxide moieties and that therefore, the single chain surfactants may have to be used in larger amounts than the branched chain surfactants to produce the emulsion and micellar formulation of this invention.

Examples of nonionic surfactants of this invention include, but are not limited to, polyethylene glycol, derivatives of phosphatidylethanolamine and synthetic detergents commercially available under the brand names Span,

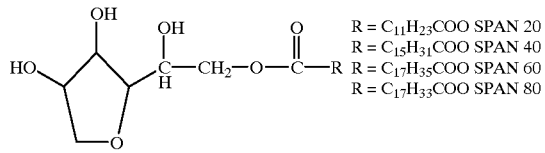

Brij,
$CH_3(CH_2)_y$—$(OCH_2CH_2O)x$—OH
Brij 72 y=17 x=2
Brij 76 y=17 x=10
Brij 78 y=17 x=20
Brij 100 y=17 x=100
Tween,

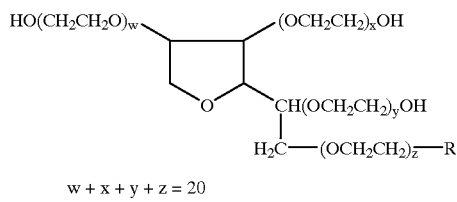

F68 and F127,

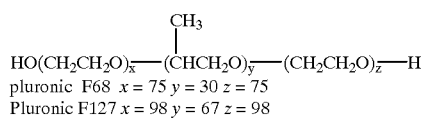

Triton X-100 and Triton x-114

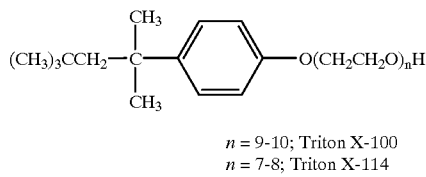

Preferred surfactants are branched chain surfactants such as Tween 20, Tween 40, Tween 60 and Tween 80.

When optionally added to the emulsion and micellar formulations of this invention, the neutral phospholipid component may be a single neutral phospholipid or a mixture of neutral phospholipids. Examples of neutral phospholipids which may be optionally added to the formulations of this invention include, but are not limited to, phosphatidylcholine (PC) or phosphatidylethanolamine (PE) or fully saturated or partially hydrogenated phosphatidylcholines (PC) or phosphatidylethanolomines (PE) having aliphatic chains between 6 and 24 atoms in length such as dioleoyl-PC (DOPC) and dioleoyl-PE (DOPE). A preferred neutral phospholipid is DOPE.

Methods for producing the emulsion and micellar formulations of the present invention are also provided.

One method for producing emulsion formulations of this invention comprises:

(a) combining an organic solvent with an oil component, a cationic amphiphile component, a nonionic surfactant component and optionally, a neutral phospholipid component;

(b) removing the organic solvent to leave a lipid film; and (c) suspending the lipid film in an aqueous carrier to produce said emulsion formulation.

An alternative method for producing the emulsion formulations of this invention comprises:

(a) combining an oil component, a cationic amphiphile component, a nonionic surfactant component and optionally, a neutral phospholipid component; and (b) adding an aqueous carrier to the combination of components in step (a) to produce said emulsion.

Preferably, average diameters of the emulsion formulations are less than about 1000 nm, more preferably less than 800 nm, and most preferably less than 500 nm.

Preferred components of the emulsions of the present invention include phosphate-buffered saline (PBS) as the aqueous carrier, castor oil as the oil component, DC-Chol as the amphiphile component, Tween 80 as the nonionic surfactant component and optionally, phosphatidylcholine or DOPE as the neutral phospholipid component.

A method for producing the micellar formulations of this invention comprises:

(a) combining an organic solvent with a cationic amphiphile component, a nonionic surfactant component and optionally a neutral phospholipid component;

(b) removing the organic solvent to leave a lipid film; and (c) suspending the lipid film in an aqueous carrier to form said micellar formulation.

Preferably, average diameters of the micellar formulations are less than about 1000 nm, more preferably less than about 800 nm; and most preferably less than about 500 nm.

Preferred components of the micellar formulations of the present invention include phosphate-buffered saline as the aqueous carrier, DC-Chol as the amphiphile component, Tween 80 as the nonionic surfactant component and optionally, PC or DOPE as the neutral phospholipid component.

When an organic solvent is used in the above methods to produce the micellar and emulsion formulations of this invention, any organic solvent which does not leave a toxic residue following removal and which solubilizes the lipid components of the emulsion and micellar formulations of this invention is suitable for use. Examples of suitable solvents include lower alcohols, dimethoxyethane, dioxane, tetrahydrofuran, tetrahydropyran, diethylether, acetone, dimethylsulfoxide (DMSO), dimethylformamides (DMF), and halogenated hydrocarbons, such as chloroform, acetonitrile, or mixtures thereof. A preferred organic solvent is chloroform.

The organic solvent may be removed by drying the combination of step (a) under a suitable gas such as argon or nitrogen and/or under a vacuum. The dried film may then be lyophilized and stored at about −80 to about 37° C. or may be resuspended in a suitable aqueous carrier. Aqueous carriers suitable for use in this invention are non-toxic to cells and may or may not be buffered. When the carriers are buffered, suitable buffers include buffers such as citrate, carbonate, bicarbonate, acetate, Tris, glycinate and maleate. Aqueous carriers which may be used in the formulations of this invention include, but are not limited to, distilled water, normal saline solution and phosphate-buffered saline. It is to be understood that a preferred pH range for the emulsion and micellar formulations of this invention is a pH range in which the particular cationic amphiphile component present in a formulation is positively charged. Those of ordinary skill in the art would readily be able to determine such a pH range from the pKa of the cationic amphiphile component present in a particular formulation.

It is further understood that the aqueous carrier in which the lipid film is suspended may include ingredients such as stabilizers, antibiotics, or antifungal and antimycotic agents.

Once formed, the micellar and emulsion formulations may be mixed with biologically active substances to produce complexes which are stable in storage as reflected by a retention of the activity of the biologically activity substance over time or by retention of the diameter of the emulsion or micellar formulation over time.

In one embodiment, the ability of an emulsion or micellar formulation of this invention to deliver a biologically active substance to a cell may be tested by exposing cells to complexes formed between an emulsion or micellar formulation and a plasmid construct containing a reporter gene as the biologically active substance. Such reporter genes are known to those of ordinary skill in the art and include, but are not limited to, the chloramphenicol acetyltransferase gene, the luciferase gene, the β-galactosidase gene and the human growth hormone gene.

By "biologically active substance" as used throughout the specification and claims is meant a molecule, compound, or composition, which, when present in an effective amount, reacts with and/or affects living cells and organisms. It is to be understood that depending on the nature of the active substance, the active substance may either be active at the cell surface or produce its activity, such as with DNA or RNA, after being introduced into the cell.

Examples of biologically active substances include, but are not limited to, nucleic acids such as DNA, cDNA, RNA (full length MRNA, ribozymes, antisense RNA, decoys), oligodeoxynucleotides (phosphodiesters, phosphothioates, phosphoramidites, and all other chemical modifications), oligonucleotide (phosphodiesters, etc.) or linear and closed circular plasmid DNA; carbohydrates; proteins and peptides, including recombinant proteins such as for example cytokines (eg interleukins), trophic and growth or naturation factors (eg NGF, G-CSF, GM-CSF), enzymes, vaccines (eg HBsAg, gp120); vitamins, prostaglandins, drugs such as local anesthetics (e.g. procaine), antimalarial agents (e.g. chloroquine), compounds which need to cross the blood-brain barrier such as anti-parkinson agents (e.g. leva-DOPA), adrenergic receptor antagonists (e.g. propanolol), anti-neoplastic agents (e.g. doxorubicin), antihistamines, biogenic amines (e.g. dopamine), antidepressants (e.g. desipraminel, anticholinergics (e.g. atropine), antiarrhythmics (e.g. quinidine), antiemetics (e.g. chloroprimamine) and analgesics (e.g. codeine, morphine) or small molecular weight drugs such as cisplatin which enhance transfection activity, or prolong the life time of DNA in and outside the cells.

When the biologically active substance is an antigenic protein or peptide, the complexes formed by the emulsion or micellar formulations of the present invention may be utilized as vaccines. In this embodiment, the presence of oil in the emulsion formulation may enhance an adjuvant effect of the complex.

Preferred biologically active substances are negatively charged substances such as nucleic acids, negatively charged proteins and carbohydrates including polysaccharides, or negatively charged drugs.

In a more preferred embodiment the biologically active substances are nucleic acids and in a most preferred embodiment, the nucleic acids are nucleic acids which encode a gene or a gene fragment or which effect transcription and/or translation.

The complexes of the present invention may be utilized to deliver biologically active substances to cells in vitro or in vivo.

When the biologically active substance is a nucleic acid, it is believed that the cationic amphiphile binds to the negatively charged nucleic acid. Preferably, nucleic acid:emulsion complexes of this invention to be used in vitro or in vivo have a weight ratio of nucleic acid: total lipid components in the emulsion of about 1:1 to about 1:50, more preferably a weight ratio of nucleic acid:total lipid components in the emulsion of about 1:1 to about 1:30 and most preferably, a weight ratio of nucleic acid:total lipid components in the emulsion of about 1:1 to about 1:20. Thus for example, in Example 11 where a DNA:emulsion complex was formed by combining 100 µg of DNA with a volume of emulsion formulation #21 containing 1100 µg total lipid components, the weight ratio of DNA:total lipid components of emulsion #21 in the complex was 100 µg/1100 µg or 1:11.

Preferably, nucleic acid:micelle complexes of this invention to be used in vitro or in vivo have a weight ratio of nucleic acid:total lipid components in the micelle of about 1:1 to about 1:50, more preferably a weight ratio of nucleic acid:total lipid components in the micelle about 1:1 to about 1:30 and most preferably a weight of nucleic acid:total lipid components of the micelle ratio of about 1:1 to about 1:20. Thus for example, in Example 11 where a DNA:micelle complex was formed by combining 100 µg of DNA with a volume of micellar formulation #31 containing 700 µg total lipid components, the weight ratio of DNA:total lipid components of micelle #31 in the complex was 100 µg/700 µg or 1:7.

It is to be understood that the combining of emulsion or micellar formulations with a nucleic acid to form the nucleic acid:emulsion or nucleic acid:micellar complexes of this invention may be carried out for at least 5 minutes in the presence or absence of serum at a temperature from about 4° C. to about 37° C. The resultant nucleic acid:emulsion and nucleic acid:micelle complexes may then be immediately used in vitro or in vivo or may be stored prior to use.

Preferably, average diameters of nucleic acid:emulsion or nucleic acid:micelle complexes to be used in vitro or in vivo are 100–4000 nm, more preferably 100–2000 nm and most preferably 100–1000 nm.

In one embodiment, the nucleic acid micelle and nucleic acid:emulsion complexes of this invention may be used to transfect cells with nucleic acid. Cells suitable for transfection in vitro include eukaryotic cells, including all mammalian cell lines suitable for transfection by cationic lipids, cells put into primary culture from a host, or cells resulting from passage of the primary culture.

When, for example, $10^5$ cells are transfected in vitro, transfection is carried out by exposing the cells to preferably from about 0.1 to about 5 µgs of nucleic acid:emulsion complex, more preferably to about 0.5 to from about 2 µgs of nucleic acid:emulsion complex.

When $10^5$ cells are to be transfected with nucleic acid:micelle complex, transfection is carried out by exposing the cells to preferably from about 0.1 to about 20 µgs of nucleic acid:micelle complex; more preferably to about 1 to about 10 µgs of nucleic acid:micelle complex.

As used herein, μg of nucleic acid:emulsion complex or μg of nucleic acid:micelle complex refers to the sum of the μg amount of nucleic acid and the μg amount of total lipid components in the emulsion or micellar formulation contained in the complex. For example, 5 μg of nucleic acid:emulsion complex might contain 0.5 μg of nucleic acid and 4.5 μg of total lipid components of emulsion formulation.

Those of ordinary skill in the art would readily understand that the total amount of nucleic acid:emulsion or nucleic acid:micelle complex to be used varies directly with the number of cells to be transfected. One advantage of the emulsion and micellar formulations of this invention over prior art cationic lipid vectors is that the emulsions and micelles of the invention, when complexed with nucleic acid, are more effective for transfecting cells cultured in serum-containing medium.

The present invention therefore relates to the use of the nucleic acid:emulsion and nucleic acid:micelle complexes of this invention to deliver nucleic acids to cells in an animal or human in vivo. Thus, the present invention also relates to the use of nucleic acid:emulsion or nucleic acid:micelle complexes as delivery systems in gene therapy.

Suitable routes of administration of the nucleic acid containing complexes of this invention to an animal or human include inoculation or injection by, for example, intravenous, oral, intraperitoneal, intramuscular, subcutaneous, intra-aural, intraarticular or intra-mammary routes, topical application, for example on the skin, scalp, ears or eyes and by absorption through epithelial or mucocutaneous linings, for example, nasal, oral, vaginal, rectal and gastrointestinal among others, and as an aerosol. Those of ordinary skill in the art would readily understand that the mode of administration may determine the sites in the organism to which the biologically active substance will be delivered and may effect the amount of complex to be administered.

Since as shown in Example 11, administration of approximately 4 μg of nucleic acid:emulsion or nucleic acid:micelle complex/gram of body weight to a 25 gram mouse produced transfection activity in vivo, those of ordinary skill in the art using this ratio of 4 μg of complex/gram of mouse body weight could obtain other ratios of μg of complex/gram of body weight which are optimized for transfection activity in other animals or humans.

In an alternative embodiment, the emulsion and micellar formulations themselves may bind with biomacromolecules (i.e. molecules produced by the animal or human) in situ after systematic or topical administrations and behave as a local depot for endogenous bioactive substances.

All articles or patents referenced herein are incorporated by reference. The following examples illustrate various aspects of the invention but are in no way intended to limit the scope thereof.

EXAMPLES

Material and Methods

Materials:

DC-Chol cationic lipid was synthesized according to Gao and Huang (*Biochem. Biophys. Res. Commun.,* 179:280–285, 1991). Tween 80 and castor oil were obtained from Fisher, pluronic co-polymer L63 was obtained from BASF. Brij, Span, and pluronic F68 and F127 surfactants were purchased from Sigma. Dioleoyl phosphatidylethanolamine (DOPE) and egg phosphatidylcholine (PC) were obtained from Avanti Polar Lipids. LipofectAMINE liposomes (DOSPA (2, 3-dioleyloxy-N-[2(spermine carboxamido)ethyl]-N,N,-dimethyl-1- propanaminium) and DOPE) in a weight ratio of 3:1) were obtained from Life Technologies, Inc.

Preparation of emulsions and micelles:

Tween 80 diluted in chloroform was combined with DC-Chol (micelles) and, where indicated DOPE or phosphatidylcholine; or with castor oil, DC-Chol and, where indicated, DOPE or phosphatidylcholine (emulsions) at different weight ratios. The organic solvent was then evaporated under a stream of nitrogen gas and the lipid film was vacuum desiccated at 4° C. overnight to remove residual organic solvent. One ml of phosphate buffered saline (PBS, pH 7.4) was then added and the mixture was allowed to hydrate for 1 h. The lipid suspension was then mixed with a vortex mixer and subsequently homogenized for 3–4 min using a tissue tearer at a speed of about 20,000 rpm. Average diameters of the emulsion or micelle formulations and of the DNA:emulsion or DNA:micelle complexes were measured by laser light scattering using a Coulter N4SD submicron particle sizer.

Preparation of DC-Chol/DOPE liposomes:

Unilamellar small liposomes of approximately 100 nm in diameter were prepared by microfluidization of hydrated mixture of DC-Chol and DOPE (weight ratio of 1:1) and filter sterilized. The final lipid concentration of the DC-Chol/DOPE liposomes used in the transfection experiments was 1.2 μg/μl of PBS.

Tissue culture:

Murine melanoma BL6 cells were cultured in RPMI medium supplemented with 10% fetal bovine serum. Human embryonic kidney 293 cells and $F_0$ were cultured in DMEM medium supplemented with 10% fetal bovine serum. CHO cells were cultured in F12 medium supplemented with 10% fetal bovine serum.

Plasmid DNA:

A $pCDNA_3$ plasmid, pCMV-Luc, containing the luciferase gene under the control of cytomegalovirus (CMV) immediate early promoter was used to assess the efficiency of transfection. A similar plasmid, pRSV-Luc, containing the same luciferase gene under the control of a Rous sarcoma virus promoter was also used to assess transfection efficiency. Plasmid pCMV-CAT is a pUC18 based plasmid containing the *E. coli* chloramphenicol acetyltransferase (CAT) gene downstream from the CMV promoter. The preparation and purification of plasmid DNA was carried out according to standard procedure (Sambrook, J., Fritsch, E. F., & Maniatis, T. Molecular Cloning: A Laboratory Manual. Cold Spring Harbor Lab Press: Plainview, 1: pp 21–52, 1989.).

Transfection:

Cells cultured in 48 well plates (about 70–80% confluent) were used for transfection and 3 wells were transfected with each formulation. The pCMV-Luc or pRSV-Luc plasmid DNAs were diluted in 125μl of serum free CHO-S-SFM medium (Life Technologies, Inc.). The emulsion, micelle, DC-Chol/DOPE liposomes or lipofectAMINE liposomes were diluted in 125 μl of Hank's balanced salt solution (HBSS). The diluted DNA and formulations or liposomes were combined, with or without the addition of fetal bovine serum to 20%, and incubated at room temperature for 5–10 min, before being added to the cells. The cells were incubated at 37° C. for 5 h. Transfection medium was replaced with growth medium containing 10% fetal bovine serum, and cells were then cultured for 2 days before the luciferase assay was performed.

Luciferase assay:

Cells were washed twice with PBS and incubated at room temperature for 10 min in the presence of 100 µl lysis buffer (0.1M Tris-HC-1, pH 7.8/0.05% Triton X-100/2 mM EDTA) and then centrifuged at 12,000×g. Ten µl of supernatant was taken for luciferase assay using the luciferase assay system (Promega) in a luminometer (AutoLumat LB953 from EG&G, Berthhold). Luciferase activity is given in relative light units (RLU).

Animal studies:

Female CD 1 mice, 5 weeks old, were purchased from Charles River Breeding Laboratories. Animal care was according to the institutional guidelines. 200 µl each of 4×concentrates (for example, the 4×concentrate of formulation #21 contained 1.0 mg oil, 1.0 mg PC, 0.5 mg Tween 80 and 3.0 mg DC-Chol per ml of PBS) of formulations #21 (1100 µg total lipid components), #28 (1100 µg total lipid components), #34 (900 µg total lipid components) and #31 (700 µg total lipid components) (600 µg DC-Chol per formulation) were mixed with 5M NaCl to a final concentration of NaCl of 0.15M and then combined with 25 µl of 4 µg/µl pCMV-CAT DNA (100 µg). The total mixture (231 µl) was injected into mice by tail vein. Two days later, mice were killed and liver, spleen, kidney, lung and heart were excised for CAT assay.

Chloramphenicol acetyltransferase(CAT) assay:

The organs excised from animals were homogenized in 40 mM Tris-HCl, pH 7.5;10 mM EDTA;150 mM NaCl. After homogenization, cells were lysed by three freeze-thaw cycles, and the lysate was heated at 65° C. for 10 min to inactive deacetylases and centrifuged for 10 min. The protein concentration of the supernatant extracts was measured with a Coomassie blue G 250-assay (Pierce). Protein was extracted from each organ and 200 µg of extract was then assayed for the CAT activity using [$^{14}$C] chloramphenicol as a substrate as previously described (Ausubel, F. M., Breht, R., Kingstone, R. E., et al. Current Protocols in Molecular Biology (Wiley, Boston), Vol. 1, pp 962–965, 1991.).

EXAMPLE 1

Physical stability of emulsion formulations and transfection ability of DNA:emulsion complexes To test which components of the emulsion formulations are important for physical stability and transfection ability, 9 different emulsion formulations containing different amounts of castor oil, egg phosphatidylcholine (PC), Tween 80 and DC-Chol were formulated. The average diameter of the formulations was measured as was their ability to transfect 293 cells by combining 6 µl of each emulsion (7.5 µg total lipid components) with 0.5 µg RSV-Luc. The resulting data are presented in Table 1.

TABLE 1

Transfection activity of DNA:emulsion complexes formed by combining DNA with different emulsion formulations

| Formulation | Composition (mg) of formulation | | | | | Average Diameter (nm) of formulation | Transfection Activity[b] (RLU × 10$^6$/well) |
| --- | --- | --- | --- | --- | --- | --- | --- |
| | Oil | PC | Tween 80 | DC-Chol | PBS (ml)[a] | | |
| #1 | 0.125 | 0.250 | 0.125 | 0.125 | 0.50 | 170 | 118 ± 22 |
| #2 | 0.250 | 0.250 | 0.250 | 0.750 | 1.20 | 151 | 444 ± 4 |
| #3 | 0.750 | 0.250 | 0.025 | 0.250 | 1.02 | 212 | 265 ± 46 |
| #4 | 0.125 | 0.125 | 0.025 | 0.750 | 0.82 | 218 | 332 ± 89 |
| #5 | 0.250 | 0.125 | 0.125 | 0.250 | 0.60 | 181 | 220 ± 7 |
| #6 | 0.750 | 0.125 | 0.250 | 0.125 | 1.00 | 154 | 68 ± 1 |
| #7 | 0.125 | 0.500 | 0.250 | 0.250 | 0.90 | 165 | 65 ± 20 |
| #8 | 0.250 | 0.500 | 0.025 | 0.125 | 0.72 | 201 | 1 ± 0.6 |
| #9 | 0.750 | 0.500 | 0.125 | 0.750 | 1.70 | 161 | 261 ± 47 |
| DC-Chol/DOPE (1:1 ratio by weight) | | | | | | 122 | 445 ± 2 |
| LipofectAMINE (DOSPA and DOPE in a 3:1 weight ratio) | | | | | | 100 | 427 ± 25 |

[a]The final concentration of the emulsion was 1.25 µg total lipid components/µl. Lipid concentrations of DC-Chol/DOPE liposome and LipofectAMINE were 1.2 µg/µl and 2.0 µg/µl respectively.
[b]293 cells were transfected with complexes formed by combining 0.5 µg of pRSV-Luc and 6 µl of emulsion (7.5 µg total lipid components) or with complexes formed by combining 0.5 µg of pRSV-Luc and 2.5 µl of DC-Chol/DOPE liposomes (3 µg lipid components) or with complexes formed by combining 0.5 µg of pRSV-Luc and 2.25 µl of lipofectAMINE liposomes (4.5 µg lipid components). Each well contained approximately 70–80 µg extractable protein.

The data show that the emulsions are physically stable with size ranging from 150 to 218 nm in average diameter as measured by laser light scattering. Further, complexes of DNA with those emulsions with high content of DC-Chol (0.750 mg), the only cationic component in the emulsion, showed high transfection activity comparable to that of the cationic DC-Chol/DOPE and LipofectAMINE liposomes.

EXAMPLE 2

Transfection activity of DNA:emulsion and DNA:micelle complexes

Emulsion and micellar formulations which contained high content of the cationic amphiphile DC-Chol (0.75 mg or more) were complexed with pRSV-Luc DNA and examined for transfection activity in BL6 and 293 cells. The data presented in Table 2

TABLE 2

Transfection activity of DNA:emulsion and DNA:micelle complexes

| Formulation | Composition (mg) of formulation | | | | | | PBS (ml)[a] | Average Diameter (nm) of formulation | Transfection Activity[b] | |
| --- | --- | --- | --- | --- | --- | --- | --- | --- | --- | --- |
| | Oil | PC | Tween 80 | DC-Chol | DOPE | Stearylamine | | | BL6 cells (RLU × 10³/well) | 293 cells (RLU × 10⁶/well) |
| #10 | 0.250 | 0.250 | 0.250 | 0.750 | — | — | 1.2 | 129 | 13 ± 8 | 530 ± 78 |
| #11 | 0.125 | 0.125 | 0.250 | 0.375 | — | — | 0.7 | 143 | 15 ± 4 | 546 ± 62 |
| #12 | 0.125 | 0.125 | 0.375 | 0.375 | — | — | 0.8 | 127 | 4 ± 2 | 239 ± 15 |
| #13 | 0.125 | 0.125 | 0.125 | 0.500 | — | — | 0.7 | 153 | 54 ± 34 | 708 ± 213 |
| #14 | 0.125 | 0.125 | 0.125 | 0.750 | — | — | 0.9 | 152 | 112 ± 37 | 880 ± 13 |
| #15 | — | 0.250 | 0.250 | 0.750 | — | — | 1.0 | 165 | 19 ± 2 | 861 ± 22 |
| #16 | 0.250 | — | 0.250 | 0.750 | — | — | 1.0 | 161 | 78 ± 14 | 710 ± 47 |
| #17 | 0.250 | — | 0.250 | 0.750 | 0.250 | — | 1.2 | 155 | 23 ± 10 | 463 ± 90 |
| #18 | 0.250 | 0.250 | 0.250 | — | — | 0.400 | 0.90 | 193 | 3 ± 1 | 9 ± 1 |
| #19 | — | — | 0.250 | 0.750 | — | — | 0.8 | 186 | 262 ± 104 | 806 ± 71 |
| #20 | 0.250 | 0.250 | — | 0.750 | — | — | 1.0 | 160 | 19 ± 9 | 840 ± 20 |
| DC-Chol/DOPE | | | | 0.600 | 0.600 | | 1.0 | 122 | 81 ± 40 | 221 ± 35 |

[a]The final concentration of the formulations was 1.25 μg total lipid components/μl. Lipid concentration of DC-Chol/DOPE liposome was 1.2 μg/μl.
[b]293 cells were transfected with complexes formed by combining 0.5 μg of pRSV-Luc and 6 μl of the indicated emulsion or micellar formulation (7.5 μg total lipid components) or with complexes formed by combining 0.5 μg of pRSV-Luc and 2.5 μl DC-Chol/DOPE liposomes (3.0 μg lipid components). Each well contained approximately 70–80 μg extractable protein except for #18 which contained 50 μg protein.

show that complexes of DNA with the emulsions and the two micellar formulations (#15 and #19) were active. However, the complex formed by combining DNA with formulation #18 that contained stearylamine instead of DC-Chol showed low transfection activity which may be due to the toxicity of stearylamine to cells as evidenced by the fact that the amount of protein extractable from wells transfected with complex containing formulation #18 was less than the amount of protein extractable from wells transfected with complexes containing all other formulations (see Table 2, footnote b). Of interest, the activities of a micellar (#19) and an emulsion (#14) DNA complex were high, and indeed more active, than the cationic liposome formulation (Dc-Chol/DOPE) in both cell lines.

EXAMPLE 3

Transfection activity of more DNA:emulsion and DNA:micelle complexes

The physical diameter of additional emulsion and micellar formulations was measured as was the transfection activity of complexes formed between DNA and these formulations. The results are shown in Table 3.

TABLE 3

Transfection activity of more DNA:emulsion and DNA:micelle complexes

| Formulation | Composition (mg)[a] of formulation | | | | | | Average Diameter (nm) of formulation | Transfection Activity[b] | |
| --- | --- | --- | --- | --- | --- | --- | --- | --- | --- |
| | Oil | PC | Tween 80 | DC-Chol | DOPE | Pluronic L63 | | BL6 (RLU × 10⁵/well) | 293 (RLU × 10⁷/well) |
| #21 | 0.250 | 0.250 | 0.125 | 0.750 | — | — | 137 | 228 ± 40 | — |
| #22 | 0.250 | 0.250 | 0.250 | 0.750 | — | — | 218 | 235 ± 67 | 101 ± 10 |
| #23 | 0.250 | 0.250 | 0.500 | 0.750 | — | — | 133 | 2 ± 0.4 | 11 ± 16 |
| #24 | 0.250 | 0.250 | 0.250 | 1.000 | — | — | 152 | 322 ± 76 | 104 ± 4 |
| #25 | 0.250 | 0.250 | 0.250 | 1.500 | — | — | 152 | 98 ± 28 | 34 ± 14 |
| #26 | — | 0.250 | 0.250 | 0.750 | — | — | 168 | 450 ± 11 | 122 ± 40 |
| #27 | 0.250 | — | 0.125 | 0.750 | — | — | 163 | 426 ± 83 | 130 ± 26 |
| #28 | 0.250 | — | 0.125 | 0.750 | 0.250 | — | 169 | 645 ± 219 | 34 ± 1 |
| #29 | 0.250 | 0.250 | — | 0.750 | — | — | 146 | 117 ± 44 | 56 ± 4 |
| #30 | — | — | 0.250 | 0.750 | — | — | 202 | 759 ± 65 | 94 ± 58 |
| #31 | — | — | 0.125 | 0.750 | — | — | 179 | 324 ± 22 | 188 ± 40 |
| #32 | — | — | — | 0.750 | — | 0.250 | 204 | 150 ± 45 | 88 ± 20 |
| #33 | — | — | — | 0.750 | — | 0.500 | 212 | 107 ± 32 | 82 ± 16 |
| #34 | — | — | 0.125 | 0.750 | 0.250 | — | 200 | 890 ± 35 | — |
| DC-Chol/DOPE | | | | | | | 122 | 1033 ± 204 | 40 ± 13 |

[a]1 ml of PBS was added to each formulation. The concentration of DC-Chol in each formulation was 0.75 mg/ml except #24 and #25 in which the DC-Chol concentrations were 1.0 mg/ml and 1.5 mg/ml respectively. However, the total lipid concentration of each formulation was different.
[b]Cells were transfected with complexes formed by combining 0.5 μg of pCMV-Luc and 6 μl of each formulation (4.5 μg DC-Chol per 6 ul of each formulation) or with complexes formed by combining 0.5 μg pCMV-Luc and 2.5 μl of DC-Chol/DOPE liposomes (3.0 μg lipid components). Each well contained approximately 70–80 μg extractable protein.

The results show that complexes of DNA and micelles containing DC-Chol and Tween 80 (#30 and #31), were again quite active and replacing Tween 80 with pluronic L63 (#32 and #33) did not significantly alter the average diameters of the formulations or their transfection activity in 293 cells. Another micelle containing DC-Chol, Tween 80 and PC (phosphatidylcholine) (#26) was also active. The remaining formulations (#22–25, 27–29) were emulsions which contained castor oil. Complexes of DNA and these emulsion formulations were fairly active in transfection. When complexes of DNA and these micellar and emulsion formulations were tested in another cell line (BL6 mouse melanoma cells), qualitatively similar results were obtained except the activity in this cell line was generally lower than that of the 293 cells. The transfection activities of complexes of DNA and these emulsions and micelles were comparable to that of the cationic liposome formulation (DC-Chol/DOPE) in 293 cells, but somewhat lower in BL6 cells.

EXAMPLE 4

Optimization of transfection conditions:

To optimize the transfection activity of the DNA:emulsion and DNA:micelle complexes, the amount of DC-Chol in each emulsion or micelle formulation was kept constant at 4.5 μg (6 ul of formulations #s 21, 27, 28 and 30,

EXAMPLE 5

Sensitivity of transfection activity of DNA:emulsion and DNA:micelle complexes to serum All the above described transfection experiments were carried out in a serum-free medium. Therefore, to determine the sensitivity of transfection activity of DNA/emulsion and DNA/micelle complexes to the presence of serum, BL6 cells were transfected in the medium containing 0 or 20% fetal bovine serum with complexes of DNA and 10 different emulsions or micelles (or DC-Chol/DOPE liposomes) as follows.

Different formulations of the compositions shown in Table 4 were prepared in a total volume of 1 ml PBS (pH 7.4). BL6 cells in a 48 well plate were then transfected with 2 μg of pCMV-Luc and 16 μl of each formulation (containing 12 μg DC-Chol), or with 2 μg of pCMV-Luc and 16 μl of DC-Chol/DOPE liposomes (1.2 μg/μl), in medium containing either 0 or 200 fetal bovine serum and luciferase activity was detected. Each well contained approximately 70–80 μg extractable protein. The results are shown in Table 4

TABLE 4

Transfection Activity Of Additional DNA:emulsion and DNA:micelle complexes

| FORMULATION | COMPOSITION (mg)[a] of formulation | | | | | LUCIFERASE ACTIVITY (RLU/well × $10^7$) | |
|---|---|---|---|---|---|---|---|
| | Oil | PC | DOPE | Tween 80 | DC-Chol | −Serum | +Serum (20%) |
| #35 | 0.25 | 0.25 | — | 0.125 | 0.75 | 14 ± 3 | 49 ± 2 |
| #36 | — | 0.25 | — | 0.125 | 0.75 | 32 ± 6 | 98 ± 6 |
| #37 | 0.25 | — | — | 0.125 | 0.75 | 170 ± 7 | 5 ± 3 |
| #38 | 0.25 | 0.25 | — | — | 0.75 | 24 ± 0.8 | 56 ± 13 |
| #39 | 0.25 | 0.25 | — | 0.125 | — | 0 | 0 |
| #40 | 0.25 | — | 0.25 | 0.125 | 0.75 | 50 ± 3 | 151 ± 6 |
| #41 | 0.25 | — | 0.25 | — | 0.75 | 40 ± 5 | 85 ± 8 |
| #42 | — | — | 0.25 | 0.125 | 0.75 | 140 ± 5 | 267 ± 44 |
| #43 | — | — | — | 0.125 | 0.75 | 156 ± 13 | 298 ± 42 |
| #44 | — | — | — | 0.25 | 0.75 | 259 ± 12 | 307 ± 8 |
| DC-Chol/DOPE liposomes | — | — | 0.60 | — | 0.60 | 107 ± 21 | 47 ± 9 |

[a]The average diameter of each formulation was 100–250 nm.

respectively were used; refer to Table 3 for compositions of formulations) and the amount of pCMV-Luc DNA was varied from 0 to 5 μg. As shown in FIG. 1, complexes of DNA and formulations #27 and #30 (refer to Table 3 for compositions) showed a maximal transfection activity in BL6 cells at 2 μg DNA while complexes of DNA and formulations #21 and #28 showed a maximum activity at 1.5 μg DNA.

Figure 2:
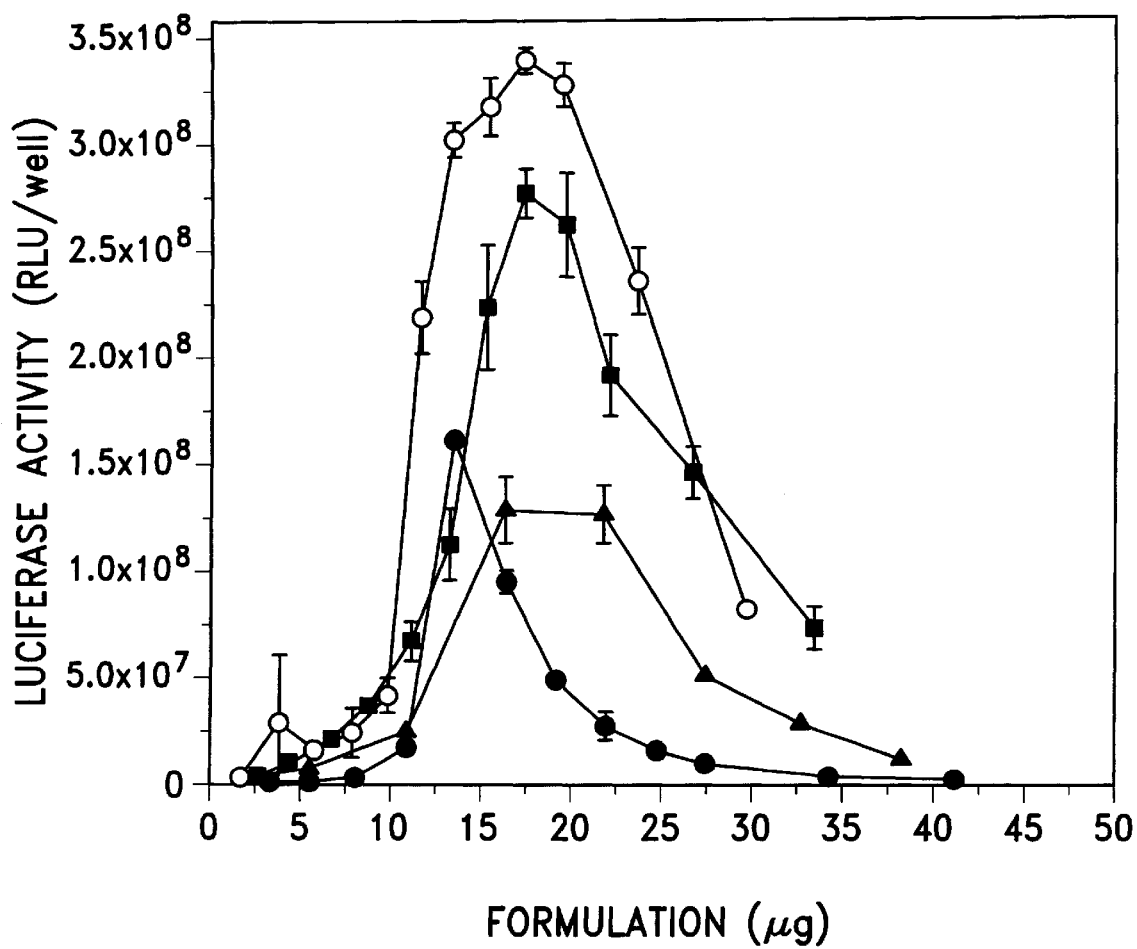
FIG. 2 shows the optimization of transfection of BL6 cells with complexes formed between pCMV-Luc DNA and varying amounts of formulations #21 (●—●), #27 (■—■), #28 (▲—▲) or #30 (○—○) as indicated on the horizontal axis (see Table 3 for compositions of formulations). The amount of pCMV-Luc DNA was fixed at 2 µg for formulations #27 and #30 and at 1.5 µg pCMV-Luc DNA for formulations #21 and #28 and "µg formulation" on the horizontal axis refers to µgs of total lipid components present in the amount of formulation combined with pCMV-Luc DNA to form complex.

Next, the amount of pCMV-Luc DNA was fixed at 2 μg for formulations #27 and #30 and at 1.5 μg for formulations #21 and #28 and complexes of DNA and varying amounts of emulsion or micelle formulation as indicated on the horizontal axis of FIG. 2 (where μg formulation on the horizontal axis refers to μg total lipid components present in the volume of formulation combined with pCMV-Luc DNA to form complex) were produced. The results presented in FIG. 2 show that complexes of DNA and formulations #27, #28 and #30 exhibited a relatively broad peak of activity in BL6 cells with the optimal amount of total lipid components present in the volume of formulation combined with DNA to produce complex being about 18 μg. However, complexes of DNA and formulation #21 exhibited a narrower peak of activity with the optimal amount of total lipid components present in the volume of formulation combined with DNA to produce complex being about 13 μg.

demonstrate that the transfection activity of DC-Chol/DOPE liposomes was quite sensitive to serum (only about 330 activity remained in the presence of serum) while of the 10 formulations tested, only complex of DNA and formulation #37 showed serum sensitivity where serum sensitivity is a reduction in transfection activity in the presence of serum relative to the level of activity observed in the absence of serum. In addition, the fact that complex of DNA and formulation #39 showed no activity in the presence or absence of serum demonstrated that the presence of cationic amphiphile is critical to transfection activity. Particularly interesting are complexes of DNA and formulations #35, #36 and #40 (corresponding in composition to formulations 21, #34 and #28 respectively in Table 3) which, of the formulations tested, exhibited the greatest enhancement of transfection activity in the presence of serum.

EXAMPLE 6

Sensitivity Of Transfection Activity Of Complexes Of DNA and Selected Formulations To Serum In Different Cell Lines To determine if the serum sensitivity observed in BL6 cells in Table 4 was observed in other cell lines, $F_0$ cells, CHO cells and 293 cells were transfected with 16 μl of selected formulations (each containing 12 μg DC-Chol/16 μl) from Table 4 combined with 2 μg of pCMV-Luc DNA or, with 16 μl DC-Chol/DOPE liposomes (1.2 μg/μl) combined with 2 μg of pCMV-Luc DNA, in medium containing 0 or 20% serum as in Example 5. The results of these experiments are shown in Table 5. The data show that complexes of DNA and all formulations are active in transfecting cells and are in general, serum-resistant.

Emulsions containing different surfactants were prepared in 1 ml of PBS containing 0.25 mg of oil, 0.25 mg of DOPE, 0.75 mg of DC-Chol and different amounts of the indicated surfactants where the total amount of surfactant used in each formulation was approximately the same by mole. BL6 cells were then transfected with 2 μg of pCMV-Luc DNA combined with 16 μl of formulation (12 μg DC-Chol/16 μl of each formulation) and assayed for luciferase activity. The results of this experiment are shown in Table 6.

TABLE 5

Transfection Activity of Complexes Of DNA And Selected Formulations in Different Cell Lines.

| FORMULATION | LUCIFERASE ACTIVITY (RLU/Well × $10^7$) | | | | | |
|---|---|---|---|---|---|---|
| | $F_0$ Cells | | CHO Cells | | 293 Cells | |
| (w/w) | −Serum | +Serum | −Serum | +Serum | −Serum | +Serum |
| #35 (Oil/PC/Tw/DC-Chol) (2:2:1:6)[a] | 8.3 ± 3.7 | 13.2 ± 7.0 | 8.0 ± 0.7 | 5.9 ± 0.4 | 33.0 ± 7.8 | 37.0 ± 3.4 |
| #37 (Oil/Tw/DC-Chol) (2:1:6:)[b] | 2.7 ± 0.2 | 1.6 ± 0.9 | 1.6 ± 1.6 | 10.4 ± 1.3 | 33.3 ± 11.3 | 44.2 ± 1.2 |
| #40 (Oil/DOPE/Tw/DC-Chol) (2:2:1:6)[c] | 8.7 ± 2.1 | 12.0 ± 2.1 | 0.4 ± 0.0 | 7.5 ± 0.4 | 27.9 ± 7.0 | 34.7 ± 2.1 |
| #44 (Tw/DC-Chol) (2:6)[d] | 22.0 ± 3.3 | 13.2 ± 1.1 | 0.4 ± 0.1 | 1.5 ± 0.3 | 68.0 ± 17.0 | 168.0 ± 17.0 |
| DOPE/DC-Chol liposomes (1:1)[e] | 2.7 ± 0.2 | 0.5 ± 0.1 | 1.7 ± 0.0 | 2.8 ± 0.5 | 88.0 ± 3.9 | 67.0 ± 3.9 |

[a]2:2:1:6 = 0.25 mg/0.25 mg/0.125 mg/0.75 mg per ml of solution.
[b]2:1:6 = 0.25 mg/0.125 mg/0.75 mg per ml of solution.
[c]2:2:1:6 = 0.25 mg/0.25 mg/0.125 mg/0.75 mg per ml of solution.
[d]2:6 = 0.25 mg/0.75 mg per ml of solution.
[e]1:1 = 0.6 mg/0.6 mg per ml of solution.

EXAMPLE 7

Stability of DNA:emulsion and DNA:micelle complexes

Figure 3:
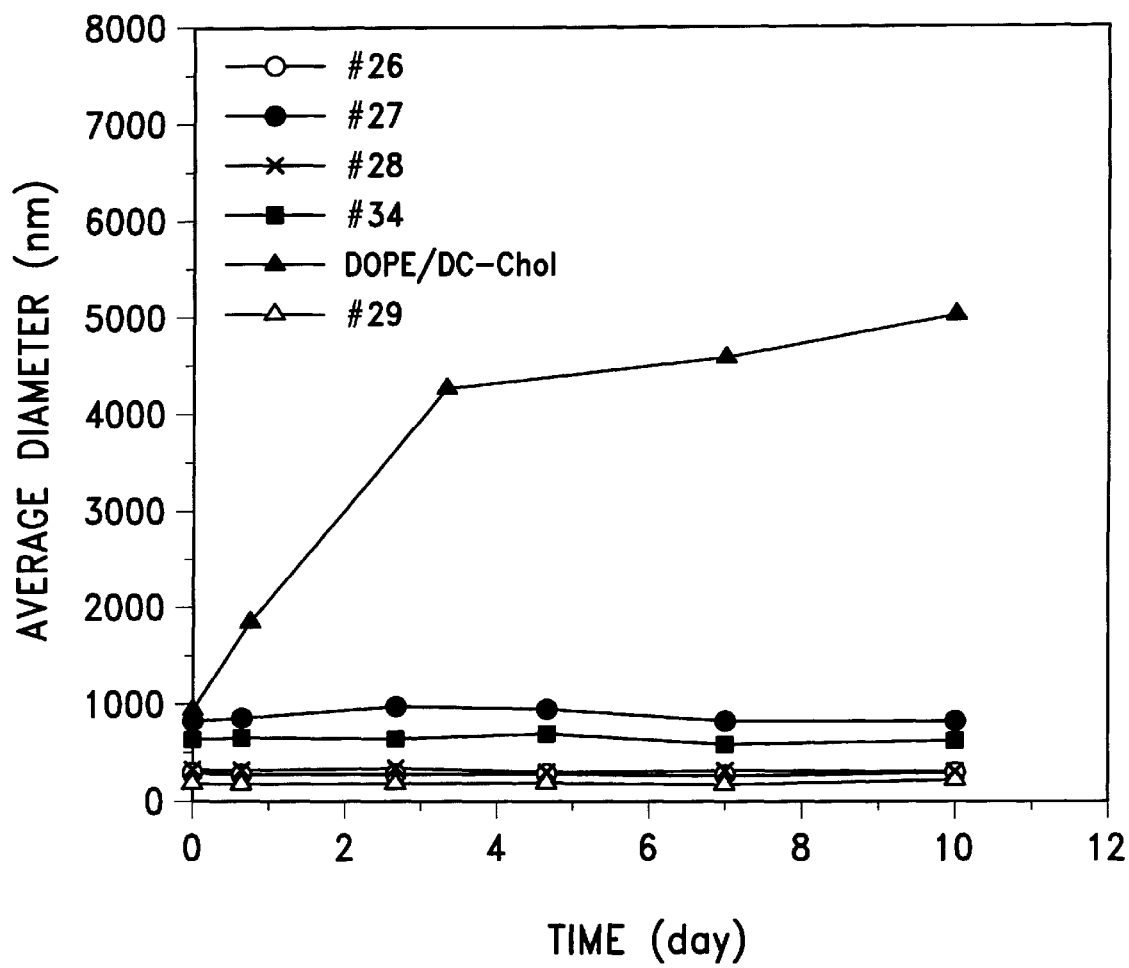
FIG. 3 shows the stability of the complexes formed between DNA and the indicated emulsion or micellar formulations (see Table 3 for composition of formulations). Complex was prepared with 2 µg of pCMVCAT and 16 µl of the indicated formulations containing the same amount of DC-Chol (12 µg) in a final volume of 250 µl, except for the DC-Chol/DOPE liposome:DNA complexes which were prepared with 1 µg pCMVCAT and 6 µg liposome in a final volume of 250 µl.

Five different formulations (#'s 26, 27, 28, 29 and 34 of Table 3) were tested for the stability of their complex with DNA. Complex was prepared by combining 2 μg pCMV-CAT DNA and 16 μl of the indicated emulsion or micelle formulation (where 16 μl of each formulation contained the same amount of DC-Chol, 12 μg) or by combining 1 μg pCMV-CAT DNA and 6 μg of DC-Chol/DOPE liposomes. As can be seen in FIG. 3, formulations #26 #28 and #29 formed relatively small complexes with DNA; the average diameter of the complex as measured by laser light scattering ranged from 200–300 nm, and remained small even after 10 days at 4° C. Formulation #34 and #27, on the other hand, formed larger complexes with DNA with average diameters of 600 and 900 nm, respectively. In contrast, DC-Chol/DOPE liposomes had formed large aggregates (1,800 nm on day 1) which had grown to even larger ones (>4,000 nm) on day 3 and subsequently precipitated out of solution (data not shown). Thus, all new formulations could form complexes with DNA that had physical stability better than that of complexes formed with the DC-Chol/DOPE liposomes.

EXAMPLE 8

Effect of Different Surfactants on the Transfection Activity of Complexes of DNA and Emulsions Composed of Oil/DOPE/DC-Chol/Surfactant in a Weight Ratio of 2:2:6:x

TABLE 6

Effect Of Different Surfactants On The Transfection Activity Of Complexes Of DNA and Emulsions Composed Of OIL/DOPE/DC-Chol/surfactant (0.25 mg: 0.25 mg: 0.75 mg: X mg per ml of PBS)

| | | | LUCIFERASE ACTIVITY (RLU/Well) × $10^7$ | |
|---|---|---|---|---|
| Surfactant | | X (mg) | −Serum | +Serum (20%) |
| Tween | 20 | 0.117 | 1.9 ± 0.4 | 4.9 ± 1.1 |
| | 40 | 0.122 | 1.9 ± 0.3 | 5.3 ± 0.7 |
| | 60 | 0.125 | 3.2 ± 0.3 | 5.6 ± 2.0 |
| Brij | 72 | 0.034 | 7.0 ± 0.7 | 10.0 ± 2.0 |
| | 74 | 0.068 | 9.4 ± 1.6 | 6.5 ± 0.3 |
| | 76 | 0.110 | 5.4 ± 0.8 | 0.08 ± 0.03 |
| | 100 | 0.446 | 0.3 ± 0.2 | 0.003 ± 0.006 |
| Span | 20 | 0.033 | 1.2 ± 0.0 | 0.1 ± 0.0 |
| | 40 | 0.038 | 1.9 ± 0.1 | 0.1 ± 0.0 |
| | 60 | 0.041 | 1.4 ± 0.4 | 0.3 ± 0.1 |
| | 80 | 0.041 | 1.4 ± 0.4 | 0.3 ± 0.1 |
| pluronic F | 68 | 0.802 | 7.8 ± 0.3 | 9.0 ± 1.4 |
| pluronic F | 127 | 1.202 | 7.9 ± 0.9 | 9.9 ± 1.1 |

Of the surfactants tested, complexes formed from emulsions containing Tween 20, Tween 40, Tween 60, Brij 72, Brij 74, F68 or F127 demonstrated transfection activity that was not sensitive to the presence of 200 serum and complexes formed from formulations containing the Tween series of detergents showed the greatest increase in transfection activity in the presence of serum relative to that observed in the absence of serum.

EXAMPLE 9

Figure 4:
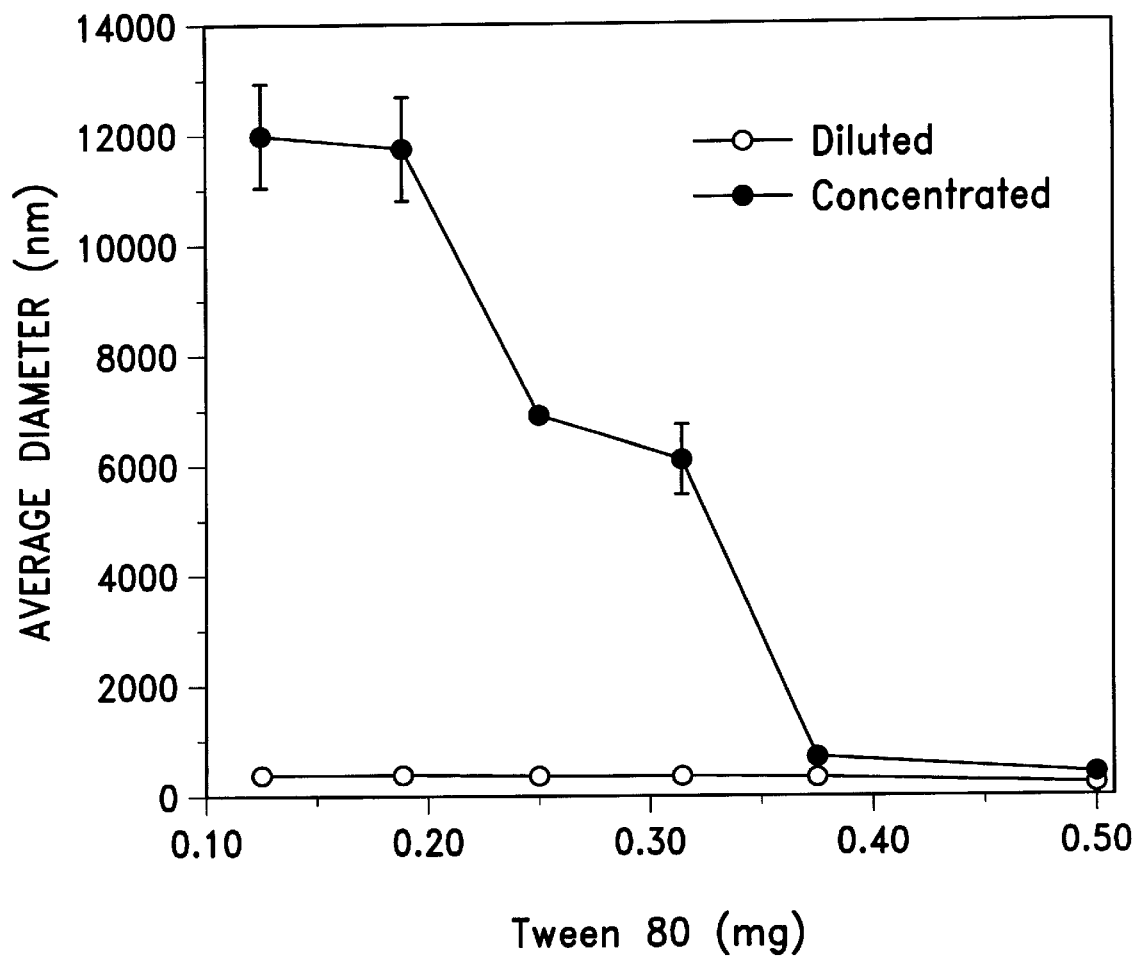
FIG. 4 shows the effect of varying the concentration of Tween 80 in emulsions containing 0.25 mg oil, 0.25 mg DOPE, 0.75 mg DC-Chol and x mg Tween 80 per ml on the average diameter of concentrated ((●—●) and diluted (○—○) pCMV-Luc DNA/emulsion complexes.

Effect of Tween 80 Concentration in Emulsions On the Average Diameters of Concentrated and Diluted DNA/Emulsion Complexes Concentrated DNA/emulsion complex was formed by adding 2 μl of solution containing 8 μg of DNA (pCMV-Luc) directly to 72 μl of emulsions containing 0.25 mg Oil/0.25 mg DOPE/0.75 mg DC-Chol and varying mg amounts of Tween 80 per ml. As in the prior examples diluted DNA/emulsion complex was formed by combining 2 μg of DNA in 125 μl with 18 μl of the same emulsions used in the concentrated complex but diluted to 125 μl. The average diameters of the concentrated and diluted complexes were measured 1 hour after incubation at room temperature. The results shown in FIG. 4 demonstrate that increasing amounts of Tween 80 reduced the size of the concentrated complexes but had no effect on the size of the diluted complexes.

EXAMPLE 10

Figure 5A:
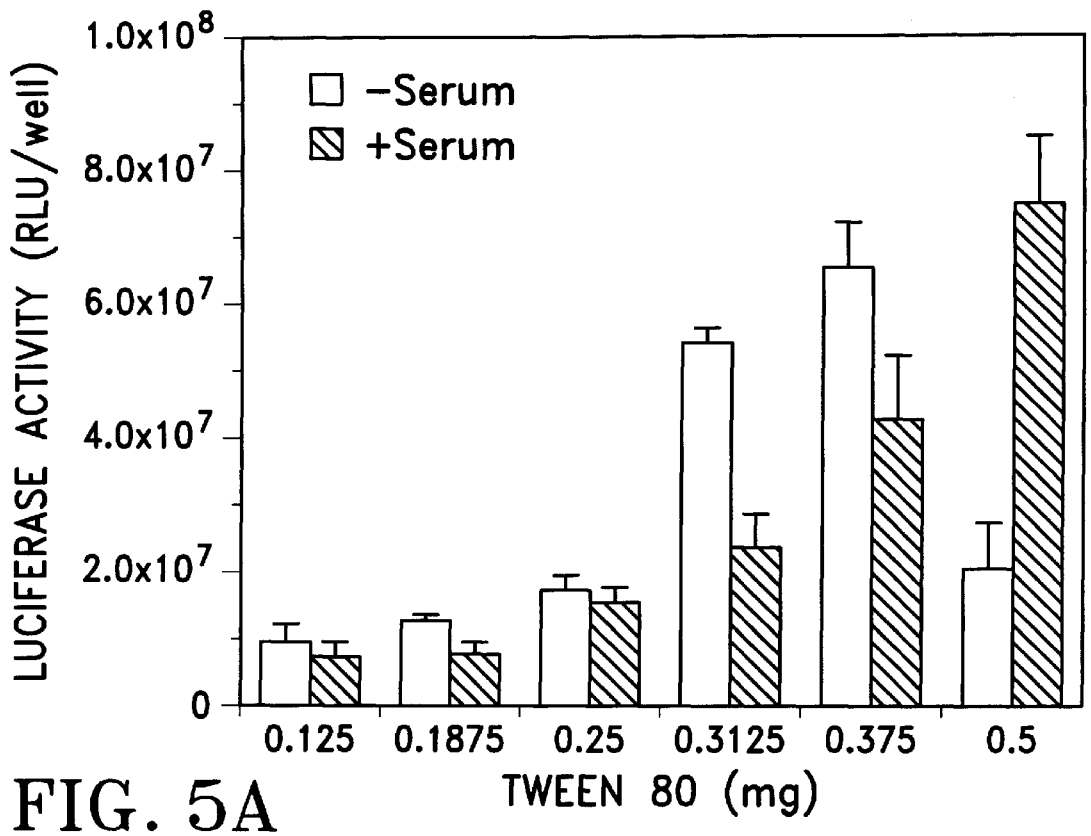
FIGS. 5A and 5B show the effect of Tween 80 on the transfection activity of concentrated (FIG. 5A) and diluted (FIG. 5B) pCMV-Luc DNA/emulsion complexes in BL6 cells in medium containing either 0 or 20% serum. The emulsion formulations used to produce the diluted and concentrated DNA:emulsion complexes contained 0.25 mg oil, 0.25 mg DOPE, 0.75 mg DC-Chol and varying amounts of Tween 80 per ml. Concentrated DNA/emulsion complex was formed by adding 2 µl of solution containing 8 µg of pCMV-Luc DNA to 72 µl of emulsion and diluted DNA/emulsion complex was formed by combining 2 µg of pCMV-Luc DNA in 125 µl with 18 µl of emulsion diluted to 125 µl.
Figure 5B:
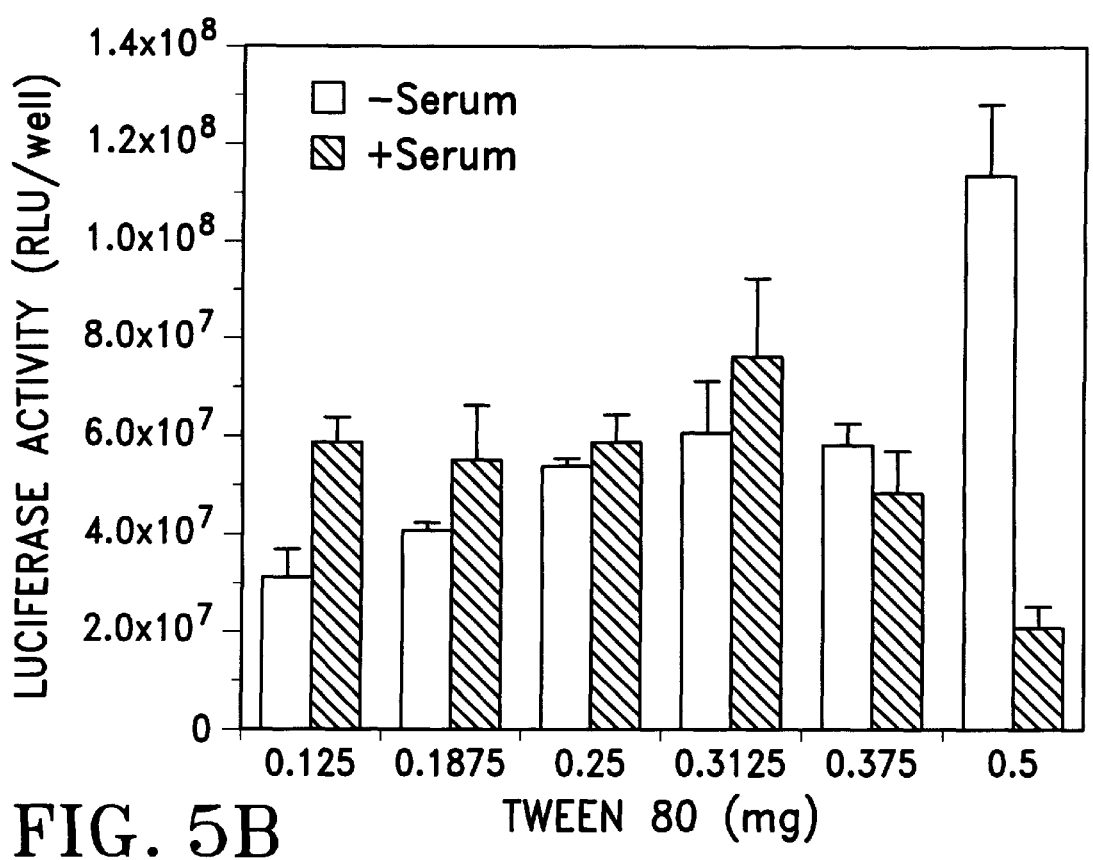

Effect of the Amount of Tween 80 in an Emulsion on Transfection Activity of Concentrated and Diluted DNA/Emulsion Complexes in the Presence or Absence of 20% Serum Emulsions and concentrated and diluted pCMV-Luc DNA/emulsion complexes were prepared as in Example 9 and the transfection activity of the complexes was measured in BL6 cells in the presence or absence of 20% serum. The results of these experiments are shown in FIGS. 5A (concentrated complex) and 5B (diluted complex). While the diluted complexes appear to show better activity than the concentrated complexes, the need to keep the volume of complex administered to an animal small may favor the use of more concentrated complexes in vivo.

EXAMPLE 11

Animal studies with DNA:emulsion and DNA:micelle Complexes

Figure 6:
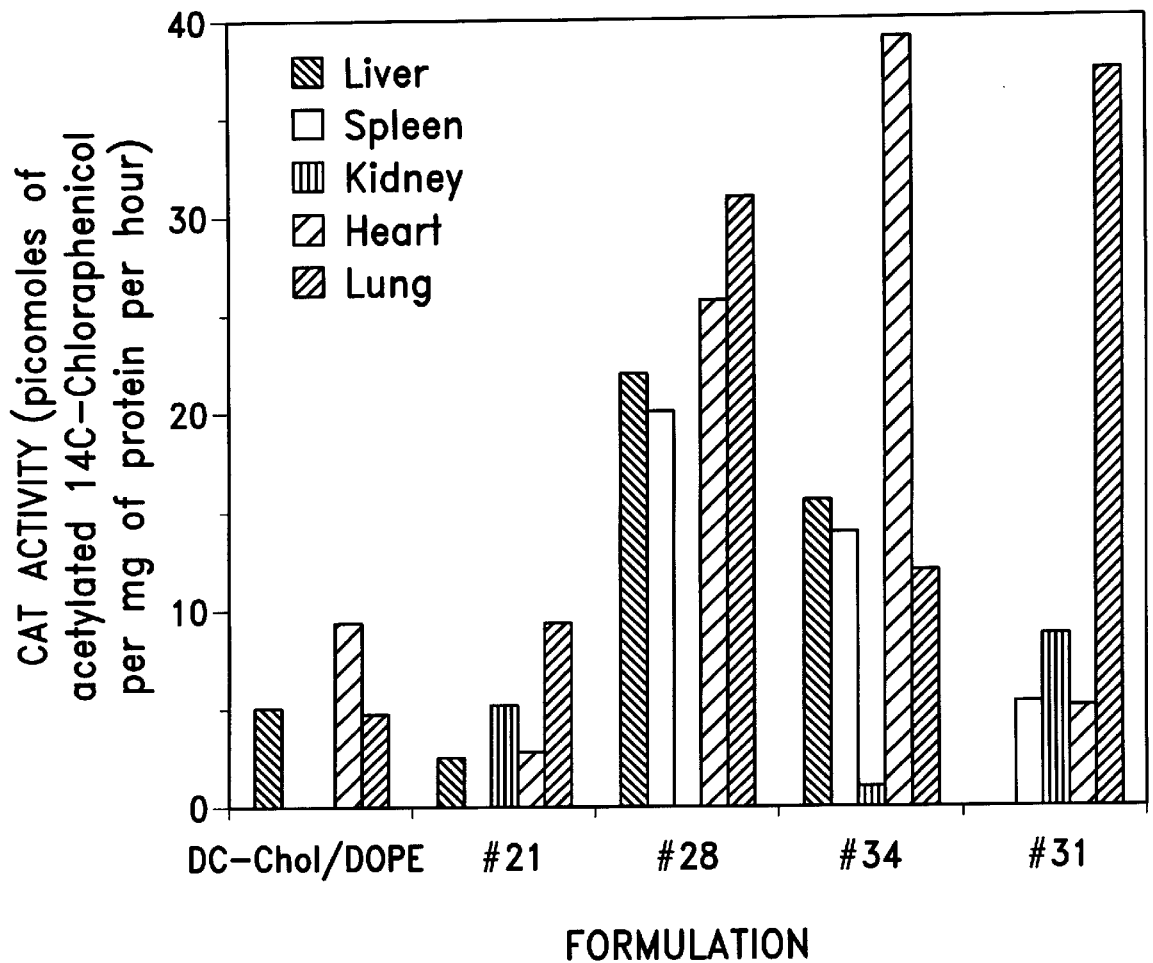
FIG. 6 shows CAT reporter gene expression in mice injected via the tail vein with DNA:emulsion or DNA:micelle complexes. The complexes were formed as follows: 200 µl each of 4× concentrates of formulations #21 (1100 µg total lipid components), #28 (1000 µg total lipid components), #34 (900 µg total lipid components) and #31 (700 µg total lipid components) were mixed with 6 µl of 5M NaCl to a final concentration of NaCl of 0.15M and then combined with 25 µl of 4 µg/µl pCMV-CAT.DNA (100 µg). The amount of DC-Chol contained in each DNA:emulsion and DNA:micelle complex was 600 µg. After two days, organs were excised and protein was extracted. CAT activity was measured by using 0.1 µCi[$^{14}$C]chloramphenicol as substrate. Each bar represents the mean of two mice.

Formulations #21, 28, 31 and 34 (refer to Table 3 for compositions) were tested for gene transfer activity in mice. 200 μl each of 4×concentrates of formulations #21 (1100 μg total lipid components), #28 (1000 μg total lipid components), #34 (900 μg total lipid components) and #31 (700 μg total lipid components)) were mixed with 6 μl of 5M NaCl to a final concentration of 0.15M NaCl and then combined with 4 μg/μl pCMV-CAT DNA (100 μg). The complexes were then injected i.v. via the tail vein of the mouse (each mouse weighed approximately 25 grams) and CAT activity was measured in major organs two days after injection. The data presented in FIG. 6 clearly demonstrates that complexes of DNA and formulations #28 (emulsion), #31 (micelle) or #34 (micelle) could transfect various organs with relatively high activity while complex of DNA and formulation #21 (emulsion), on the other hand, was weak and comparable to that of DC-Chol/DOPE liposomes. In addition, the activity of complex of DNA and formulation #31 seems to be lung specific, as no other organs were significantly transfected; complex of DNA and formulation #28 could transfect all organs quite well with only weak transfection of the kidney, and complex of DNA and formulation #34 showed a high activity in the heart with very low activity in the kidney.

What is claimed is:

1. An oil-in-water emulsion formulation comprising lipid components, a nucleic acid and an aqueous calmer, wherein the lipid components comprise an oil component, a cationic amphiphile component, and a nonionic surfactant component;
   wherein the oil component is present in an amount from about 10 to about 80 weight % of the total lipid components in the formulation, the cationic amphiphile component is present in an amount from about 5 to about 80 weight % of the total lipid components and the nonionic surfactant component is present in an amount from about 5 to about 50 weight % of the total lipid components.

2. The formulation of claim 1 further comprising a neutral phospholipid component.

3. The formulation of claim 2, wherein the cationic amphiphile component is a lipid selected from the group consisting of 1,2 bis(oleoyloxy)-3-(trimethylammonio) propane (DOTAP), N-[l,-(2,3-dioleoyloxy) propyl]-N, N, N-trimethylammoniumchloride (DOTMA), 1,2-dioleoyl-3-(4' trimethylammonio) butanoyl-sn-glycerol (DOBT), cholesteryl (4' trimethylammonia) butanoate (ChOTB), DL-1, 2-dioleoyl-3-dimethylaminopropyl-B-hydroxyethylammonium (DORI), DL-1,2-O-dioleoyl-3-dimethylaminopropyl-β-hydroxyethylammonium (DORIE), 1,2-dioleoyl-3-succinyl-sn-glycerol choline ester (DOSC), cholesteryl hemisuccinate choline ester (ChOSC), doctadecylamidoglycyl-spermine (DOGS), dipalmitoyl phosphatidyesthanolamidospermine (DPPES), cholesteryl-3β-carboxyl-amido-ethylenetrimethylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamido-ethylenetrimethylammonium iodide, 1-dimethylamino-3-trimethylammonio-DL-2-propyl-cholesteryl-3β-oxysuccinate iodide, 2- [(2-trimethylammonio)-ethylmethylamino] ethyl-cholesteryl-3β-oxysuccinate iodide, 3β[N-(N',N'-dimethylaminoethane) carbamoyl] cholesterol (DC-Chol), and 3β-[N-(polyethyleneimine)-carbamoyl]cholesterol.

4. The formulation of claim 1 for facilitating the delivery of the nucleic acid to cells, wherein the cationic amphiphile is 3β[N-(N', N'-dimethylaminoethane) carbamoyl] cholesterol (DC-Chol).

5. The formulation of claim 1, wherein the oil component is a natural oil.

6. The formulation of claim 1, wherein the weight ratio of nucleic acid to total lipid components in the formulation is about 1:1 to about 1:50.

7. The formulation of claim 5, wherein the oil component is castor oil.

8. A method for delivering a nucleic acid to cells comprising exposing the cells to the formulation of claim 1 thereby facilitating the delivery of the nucleic acid to the cells.

9. The method of claim 8 wherein the cells are mammalian cells exposed to the formulation in the presence of serum.

10. The formulation of claim 1 wherein the formulation is suitable for transfection in vivo.

11. The method according to claim 8 wherein the cells are exposed to the formulation in vivo by administering the formulation to an animal or human in an amount effective to facilitate the delivery of the nucleic acid to the cells of the animal or human.

12. The formulation of claim 1, wherein the nonionic surfactant is a synthetic detergent.

13. The method according to claim 8 wherein the cells are exposed to the formulation in vitro.

14. The formulation of claim 12 wherein the synthetic detergent is selected from the group consisting of sorbitan fatty acid ester, sorbitan polyoxyethylene fatty acid ester, Pluronic and octoxynol surfactants.

15. An oil-in-water emulsion formulation comprising lipid components and an aqueous carrier, wherein the lipid components comprise a cationic amphiphile component, a nonionic surfactant component, and an oil component,
   wherein the oil component is present in an amount from about 10 to about 80 weight % of the total lipid components in the formulation lie cationic amphiphile component is present in an amount from about 5 to about 50 weight % of the total lipid components and the nonionic surfactant component is present in an amount from about 5 to about 50 weight % of the total lipid components, and wherein the cationic amphiphile component is selected from the group consisting of 1,2 bis(oleoyloxy)-3-(trimethylammonio)propane (DOTAP), N-[1,-(2,3-dioleoyloxy) propyl]-N, N, N-trimethyl ammonium chloride (DOTMA), 1,2-dioleoyl-3- (4' trimethylammonio) butanoyl-sn-glycerol (DOBT), cholesteryl (4' trimethylammonia) butanoate (ChOTB), DL-1, 2-dioleoyl-3-dimethylaminopropyl-B-hydroxyethylammonium (DORI), DL-1,2-O-dioleoyl-3-dimethylaminopropyl-β-hydroxyethylammonium (DORIE),1,2-dioleoyl-3-succinyl-sn-glycerol choline ester (DOSC), cholesteryl hemisuccinate choline ester (ChOSC), doctadecylamidoglycyl-spermine (DOGS), dipalmitoyl phosphatidyesthanolamidospermine (DPPES), cholesteryl-3 -carboxyl-amido-ethylenetrimethylammonium iodide, 1-dimethylamino-3-triethylammonio-DL-2-propyl-cholesteryl carboxylate iodide, cholesteryl-3β-carboxyamidoethyleneamine, cholesteryl-3β-oxysuccinamido-ethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N-(N',N'-dimethylaminoethane) carbamoyl] cholesterol (DC-Chol), and 3β-[N-(polyethyleneimine)-carbamoyl] cholesterol.

16. The formulation of claim 14 wherein the cationic amphiphile component is 3β[N-(N', N'-dimethylaminoethane) carbamoyl] cholesterol (DC-Chol).

17. The formulation of claim 1, wherein the nonionic surfactant is selected from the group consisting of nonionic surfactant derivatives of polyethylene glycol and phosphatidylethanolamine.

18. The formulation of claim 1 wherein the nucleic acid is selected from the group consisting of DNA and RNA.

19. The method of claim 11 wherein the formulation is administered to the animal or human by an intravenous, oral, intraperitoneal, intramuscular, subcutaneous, intra-aural, topical, intraarticular or intra-mammary route.

20. The formulation of claim 12 wherein the synthetic detergent is selected from the group consisting of sorbitan monolaurate, sorbitan monopalmitate, sorbitan monostearate, sorbitan monooleate, polyoxyethylene sorbitan monolaurate, polyoxyethylene sorbitan monopalmitate, polyoxyethylene sorbitan monostearate, polyoxyethylene sorbitan monooleate, poloxamer 188, poloxamer 407, polyoxyethylene (10) isooctylphenyl ether, and polyoxyethylene (8) isooctylphenyl ether.

21. The formulation of claim 1 wherein the formulation is suitable for transfection in vitro.

* * * * *

UNITED STATES PATENT AND TRADEMARK OFFICE
CERTIFICATE OF CORRECTION

PATENT NO. : 6,120,794
DATED : September 19, 2000
INVENTOR(S) : Dexi Liu et al.

It is certified that error appears in the above-identified patent and that said Letters Patent is hereby corrected as shown below:

Title page,
References Cited, U.S. PATENT DOCUMENTS, inventor "Jesse" should be
-- Jessee --; and inventor "Wolf" should be -- Wolff --.

Column 1,
Line 39, "0.70%." should be -- 0.7% --.
Line 56, "micellar-formulations" should be -- micellar formulations --.

Column 3,
Line 56, "pCMV-CAT.DNA" should be -- pCMV-CAT DNA --.

Column 4,
Line 8, "weight,-more" should be -- weight, more --.
Line 63, "about 700" should be -- about 70% --.
Line 64, "about 600%" should be -- about 60% --.

Column 9,
Line 39, "MRNA" should be -- mRNA --.
Line 54, "desipraminel" should be -- desipramine) --.

Column 13,
Line 46, "4xconcentrates" and "4xconcentrate" should be -- 4x concentrates -- and
-- 4x concentrate --, respectively.

Column 20,
Line 58, "200 serum" should be -- 20% serum --.

Column 21,
Line 56, "calmer" should be -- carrier --.

Column 22,
Line 3, "2" should be -- 1 --.
Line 64, "lie" should be -- the --.
Line 66, "50" should be -- 80 --.

UNITED STATES PATENT AND TRADEMARK OFFICE
CERTIFICATE OF CORRECTION

PATENT NO. : 6,120,794
DATED : September 19, 2000
INVENTOR(S) : Dexi Liu et al.

It is certified that error appears in the above-identified patent and that said Letters Patent is hereby corrected as shown below:

Column 23,
Line 16, "cholesteryl-3 -carboxyl" should be -- cholesteryl-3$\beta$-carboxyl --.
Line 18, "triethylammonio" should be -- trimethylammonio --.

Signed and Sealed this

Seventh Day of January, 2003

JAMES E. ROGAN
*Director of the United States Patent and Trademark Office*